United States Patent [19]

Araki et al.

[11] Patent Number: 4,868,217
[45] Date of Patent: Sep. 19, 1989

[54] BACTERICIDAL COMPOSITION

[75] Inventors: Seiichi Araki, Kakamigahara; Mamoru Suzuki, Nagoya; Tetsuji Iwasaki; Yuichi Hioki, both of Wakayama, all of Japan

[73] Assignees: Eisai Co., Ltd.; Kao Corporation, both of Tokyo, Japan

[21] Appl. No.: 33,317

[22] Filed: Apr. 1, 1987

[30] Foreign Application Priority Data

Apr. 2, 1986 [JP] Japan ................................. 61-75978

[51] Int. Cl.[4] ...................... A01N 33/12; A01N 31/14
[52] U.S. Cl. .................................... 514/642; 514/723
[58] Field of Search ........................ 514/642, 738, 723

[56] References Cited

U.S. PATENT DOCUMENTS 4,476,107 10/1984 Schmolka .............................. 424/49

FOREIGN PATENT DOCUMENTS 1554615 10/1979 United Kingdom .

OTHER PUBLICATIONS

Polyethers (PtI Polyalkylene Oxides & Other Polyethers) Gaylord ed. Interscience Publishers © 1963.

Primary Examiner—Douglas W. Robinson
Assistant Examiner—Raymond J. Henley, III
Attorney, Agent, or Firm—Flynn, Thiel, Boutell & Tanis

[57] ABSTRACT

A bactericidal composition comprises didecyldimethyl didecyldimethylammonium chloride and an alkylene oxide adduct of a polyhydric alcohol being trivalent or more and is effective bactericidally even to feces of a cattle stall.

10 Claims, No Drawings

BACTERICIDAL COMPOSITION

This invention relates to a bactericidal composition. More particularly, it relates to a bactericidal composition which exhibits a high bactericidal effect even in the presence of organic materials such as feces in a cattle stall.

It has been widely known that didecyldimethylammonium chloride exhibits higher bactericidal effects on various bacteria including pathogenic ones than other bactericidal compounds such as alkylbenzyldimethylammonium chloride.

However didecyldimethylammonium chloride has a disadvantage that its bactericidal effect is significantly lowered because of a large amount of feces adhering thereto when used in stalls of cattle, for example, cows or horses, or poultry.

Under these circumstances, we have tried to solve the above problem and to enhance the bactericidal effect of didecyldimethylammonium chloride in the presence of organic materials originating from feces. As a result, we have found that didecyldimethylammonium chloride can exhibit an excellent bactericidal effect, even in the presence of organic materials, when it is used together with a particular compound, thus completing the present invention.

The invention provides a bactericidal composition which comprises didecyldimethylammonium chloride and an alkylene oxide adduct of a polyhydric alcohol having three or more hydroxyl groups.

The polyhydric alcohol preferably includes pentaerythritol, trimethylolpropane, di-trimethylolpropane, polymethylolnonane, neopentylglycol, di-pentaerythritol, glycerine and polyglycerine. It is preferred that the adduct has a mole number of added alkylene oxide ranging between 4 and 200, more preferably 4 and 100, per one mole of the polyhydric alcohol.

The adduct includes an embodiment having the formula (I):

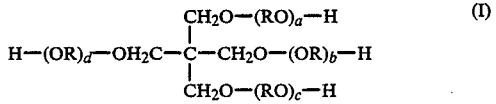

in which R is an alkylene having 2 to 4 carbon atoms, a, b, c and d each are zero or an integer of 1 to 50 and the total number of a, b, c and d ranges from 4 to 200.

The alkylene oxide adduct preferably contains 20 to 100 mole percent of ethylene oxide based on the total alkylene oxide.

The adduct to use in the invention is obtained by the addition reaction between a polyhydric alcohol having three or more hydroxyl groups and an alkylene oxide in the presence of an acid catalyst or an alkali catalyst. The alkylene oxide preferably includes ethylene oxide, propylene oxide, butylene oxide and a mixture thereof. The addition reaction may be conducted so as to obtain a block adduct.

It is preferable that a weight ratio of the didecyldimethylammonium chloride to said adduct ranges from 1/0.1 to 1/10, more preferably from 1/0.2 to 1/7.

The bactericidal composition of the present invention may be usually prepared in the form of an aqueous solution of 2 to 50% by weight in concentration and diluted prior to use to give a concentration of 100 to 1000 ppm, although it may vary depending on the subject.

In the embodiment of the present invention, various surfactants or other additives may be added to the diluted composition of the present invention to thereby improve the physical properties thereof, for example, to lower the surface tension, to impart the wet malleability or to control foaming. Examples of these additives are nonionic surfactants such as polyoxyethylene (POE) (9) nonylphenyl ether and POE (12) octylphenyl ether; and anionic surfactants such as sodium POE (5) octylphenyl ether sulfate and magnesium POE (6) dodecylphenyl ether sulfate.

The bactericidal composition of the invention provides an excellent bactericidal effect even in the presence of organic materials such as feces. This effect is synergistic due to the two components.

To further illustrate the present invention, and not by way of limitation, the following Examples will be given.

COMPARATIVE EXAMPLE 1

*Escherichia coli*, which had been previously cultured in a slant medium, was suspended in didecyldimethylammonium chloride diluted to the concentrations as shown in Table 1 for 1, 2.5 and 5 minutes. Then the cells were collected, transplanted to an agar medium and allowed to stand therein for 24 hours, followed by observation of the growth condition thereof.

The abovementioned procedure was followed except that 1% by weight of fowl droppings were added to each didecyldimethylammonium chloride solution.

The growth of the *E. coli* was evaluated according to the following criterion:
- −: no colony is formed,
- ±: 1 to 5 colonies are formed,
- +: 6 to 10 colonies are formed, and
- ++: 11 or more colonies are formed.

Table 1 shows the result.

TABLE 1

| droppings added Conc. of didecyl-dimethylammonium chloride (ppm) | No fowl droppings added contact period (min) | | | 1.0% of fowl contact period (min) | | |
|---|---|---|---|---|---|---|
| | 1 | 2.5 | 5 | 1 | 2.5 | 5 |
| 12.5 ppm | ± | − | − | ++ | ++ | ++ |
| 25.0 | − | − | − | ++ | ++ | ++ |
| 50.0 | − | − | − | ++ | ++ | ++ |
| 100.0 | − | − | − | ++ | + | + |
| 200.0 | − | − | − | + | + | ± |
| 400.0 | − | − | − | + | ± | − |

These results suggest that the bactericidal effect of didecyldimethylammonium chloride is lowered under practical conditions, i.e., in the presence of fowl droppings.

EXAMPLE 1

The compositions listed in Table 2 were each prepared, using didecyldimethylammonium chloride, an alkylene oxide adduct of a polyhydric alcohol and water. The alkylene oxide adduct was an adduct of 8 moles of ethylene oxide to pentaerythritol, called POE(8)pentaerythritol, or an adduct of 8 moles of ethylene oxide and 20 moles of propylene oxide to pentaerythritol, called POE(8)POP(20)pentaerythritol. These compositions were examined as to their effect against the growth of *E. coli* in the same way as shown in Comparative Example 1. Results are shown in Table 3.

TABLE 2

| Formulation | Content of didecyldimethyl ammonium chloride (wt. %) | Adduct Name | Adduct (wt. %) | Water (wt. %) |
|---|---|---|---|---|
| 1 | 10 | POE(8) pentaerythritol | 1 | 89 |
| 2 | 10 | | 10 | 80 |
| 3 | 10 | | 50 | 40 |
| 4 | 10 | | 70 | 20 |
| 5 | 10 | POE(8)/ POP(20) pentaerythritol | 1 | 89 |
| 6 | 10 | | 10 | 80 |
| 7 | 10 | | 50 | 40 |
| 8 | 10 | | 70 | 20 |

TABLE 3

| Dilution ratio (concn. of didecyldimethylammonium chloride) | Formulation | 1% fowl droppings added contact period (min) 1 | 2.5 | 5 |
|---|---|---|---|---|
| × 1000 (100 ppm) | 1 | + | ± | ± |
| | 2 | ± | − | − |
| | 3 | − | − | − |
| | 4 | − | − | − |
| | 5 | + | + | ± |
| | 6 | ± | − | − |
| | 7 | − | − | − |
| | 8 | − | − | − |
| × 500 (200 ppm) | 1 | ± | ± | − |
| | 2 | − | − | − |
| | 3 | − | − | − |
| | 4 | − | − | − |
| | 5 | ± | ± | − |
| | 6 | − | − | − |
| | 7 | − | − | − |
| | 8 | − | − | − |
| × 250 (400 ppm) | 1 | ± | − | − |
| | 2 | − | − | − |
| | 3 | − | − | − |
| | 4 | − | − | − |
| | 5 | ± | − | − |
| | 6 | − | − | − |
| | 7 | − | − | − |
| | 8 | − | − | − |

COMPARATIVE EXAMPLE 2

The procedure of Example 1 was followed except that the preparations were formulated, as shown below, by using POE(8) lauryl ether and POE(7) nonylphenylether for the adduct.

| Comparative Formulation 1: | |
|---|---|
| didecyldimethylammonium chloride | 10% by weight |
| POE (8) lauryl ether | 50 |
| water | 40 |

| Comparative Formulation 2 | |
|---|---|
| didecyldimethylammonium chloride | 10% by weight |
| POE (7) nonylphenyl ether | 50 |
| water | 40 |

Table 4 shows the results.

TABLE 4

| Dilution ratio (concn. of didecyldimethylammonium chloride) | Formulation | 1% fowl droppings added contact period (min) 1 | 2.5 | 5 |
|---|---|---|---|---|
| × 1000 | Comp. Form. 1 | ++ | + | + |
| (100 ppm) | 2 | ++ | + | + |
| × 500 | 1 | + | + | ± |
| (200 ppm) | 2 | + | + | ± |
| × 250 | 1 | + | ± | − |
| (400 ppm) | 2 | + | ± | − |

EXAMPLE 2

The preparations 9 to 13 were each formulated by using 10 wt.% of didecyldimethylammonium chloride, 50 wt.% of an alkylene oxide adduct listed below and 40 wt.% of water and examined about the effect against the growth of $E.\ coli$ in the same way as shown in Comparative Example 1. Results are shown in Table 5.

| preparation | |
|---|---|
| 9 | POE (10) trimethylolpropane |
| 10 | POE (15) ditrimethylolpropane |
| 11 | POE (8) POP (6) glycerine |
| 12 | POE (12) dipentaerythritol |
| 13 | POE (12) diglycerine |

TABLE 5

| Dilution ratio (concn. of didecyldimethylammonium chloride) | Formulation | 1% fowl droppings added contact period (min) 1 | 2.5 | 5 |
|---|---|---|---|---|
| × 1000 (100 ppm) | 9 | − | − | − |
| | 10 | − | − | − |
| | 11 | ± | − | − |
| | 12 | − | − | − |
| | 13 | ± | − | − |
| × 500 (200 ppm) | 9 | − | − | − |
| | 10 | − | − | − |
| | 11 | − | − | − |
| | 12 | − | − | − |
| | 13 | − | − | − |
| × 250 (400 ppm) | 9 | − | − | − |
| | 10 | − | − | − |
| | 11 | − | − | − |
| | 12 | − | − | − |
| | 13 | − | − | − |

What is claimed is:

1. A bacterial composition which comprises didecyldimethylammonium chloride and a $C_{2-4}$-alkylene oxide adduct of a polyhydric alcohol having three or more hydroxyl groups, said adduct having a mole number of $C_{2-4}$-alkylene oxide ranging between 4 to 200 per mole polyhydric alcohol and a weight ratio of didecyldimethylammonium chloride to $C_{2-4}$-alkylene oxide adduct of from 1/0.1 to 1/10.

2. A composition as claimed in claim 1, in which said polyhydric alcohol is selected from pentaerythritol, trimethylolpropane, di-trimethylolpropane, polymethylolnonane, neopentylglycol, di-pentaerythritol, glycerine and polyglycerine.

3. A composition as claimed in claim 1, in which the adduct contains 20 to 100 mole percent of ethylene oxide based on total $C_{2-4}$-alkylene oxide.

4. A composition as claimed in claim 1, which further comprises a nonionic surfactant.

5. An aqueous solution which comprises 2 to 50 percent by weight of said composition as defined in claim 1 and the balance of water.

6. A bacterial composition which comprises didecyldimethylammonium chloride and an alkylene oxide adduct of a polyhydric alcohol having the following formula (I):

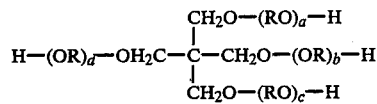

in which R is an alkylene having 2 to 4 carbon atoms, a, b, c and d each are zero or an interger of 1 to 50 and a+b+c+d ranges from 4 to 200, said didecyldimethylammonium chloride having a weight ratio to said alkylene oxide adduct of from 1/0.1 to 1/10.

7. A composition as claimed in claim 6, in which the adduct contains 20 to 100 mole percent of ethylene oxide based on total alkylene oxide.

8. A composition as claimed in claim 6, which further comprises a nonionic surfactant selected from the group consisting of polyoxyethylene (9) nonylphenyl ether and polyoxyethylene (12) octylphenyl ether.

9. An aqueous solution consisting essentially of 2 to 50 percent by weight of a bacterial composition and the balance of water, said bacterial composition comprising didecyldimethylammonium chloride and a $C_{2-4}$-alkylene oxide adduct of a polyhydric alcohol having three or more hydroxyl groups, said adduct having a mole number of $C_{2-4}$-alkylene oxide ranging between 4 to 200 per mole polyhydric alcohol and a weight ratio of didecyldimethylammonium chloride to $C_{2-4}$-alkylene oxide adduct of from 1/0.1 to 1/10.

10. An aqueous solution as claimed in claim 9, in which said bacterial composition also contains a nonionic surfactant.

* * * * *

UNITED STATES PATENT AND TRADEMARK OFFICE
CERTIFICATE OF CORRECTION

PATENT NO. : 4 868 217
DATED : September 19, 1989
INVENTOR(S) : Seiichi ARAKI et al, It is certified that error appears in the above-identified patent and that said Letters Patent is hereby corrected as shown below:

Column 5, lines 6-14; change the formula to read as follows:

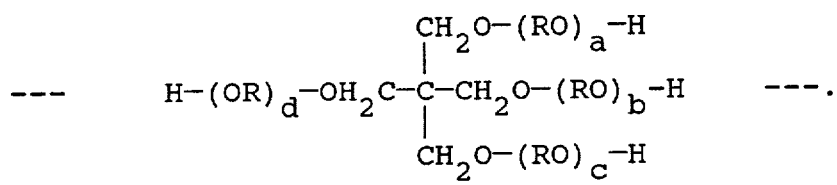

Signed and Sealed this

Thirteenth Day of November, 1990

Attest:

HARRY F. MANBECK, JR.

Attesting Officer          Commissioner of Patents and Trademarks